(12) United States Patent
Abe et al.

(10) Patent No.: US 8,481,776 B2
(45) Date of Patent: Jul. 9, 2013

(54) FUNCTIONAL SUBSTANCE-RELEASING AGENT

(75) Inventors: Hideyuki Abe, Wakayama (JP); Akiyoshi Kimura, Wakayama (JP); Makiko Shigehisa, Berlin (DE)

(73) Assignee: Kao Corporation, Tokyo (JP)

( * ) Notice: Subject to any disclaimer, the term of this patent is extended or adjusted under 35 U.S.C. 154(b) by 168 days.

(21) Appl. No.: 12/866,976

(22) PCT Filed: Mar. 12, 2009

(86) PCT No.: PCT/JP2009/055368
§ 371 (c)(1),
(2), (4) Date: Oct. 5, 2010

(87) PCT Pub. No.: WO2009/113721
PCT Pub. Date: Sep. 17, 2009

(65) Prior Publication Data
US 2011/0015421 A1  Jan. 20, 2011

(30) Foreign Application Priority Data

Mar. 14, 2008 (JP) .................................. 2008-65638

(51) Int. Cl.
*C07F 7/18* (2006.01)
(52) U.S. Cl.
USPC ........................................ 556/466; 556/483
(58) Field of Classification Search
USPC ............................... 556/466, 483; 424/401, 64
See application file for complete search history.

(56) References Cited

U.S. PATENT DOCUMENTS

| | | | | |
|---|---|---|---|---|
| 3,215,719 A | * | 11/1965 | Allen et al. | 556/482 |
| 3,253,009 A | * | 5/1966 | Allen et al. | 556/483 |
| 4,500,725 A | | 2/1985 | Yemoto et al. | |
| 4,880,851 A | | 11/1989 | Yamamoto | |
| 2004/0072704 A1 | | 4/2004 | Gerke et al. | |

FOREIGN PATENT DOCUMENTS

| | | |
|---|---|---|
| DE | 40 40 679 A1 | 6/1992 |
| EP | 0281034 A2 | 9/1988 |
| GB | 1189435 | 4/1970 |
| GB | 2007703 A | 5/1979 |
| JP | 54-59498 A | 5/1979 |
| JP | 54-93006 A | 7/1979 |
| JP | 58-22063 A | 2/1983 |
| JP | 63-260567 A | 10/1988 |
| JP | 7-268383 A | 10/1995 |
| JP | 2003-526644 A | 9/2003 |
| JP | 2005-213153 A | 8/2005 |
| WO | WO 01/79212 A1 * | 10/2001 |
| WO | WO 01/79212 A1 | 10/2001 |

OTHER PUBLICATIONS

Ozerenko, E. A., et al, Translated from Zhurnal Obshchei Khimii, 1990, 60(2), 394-399.*
Clausen R.P. et al, Journal of Organic Chemistry, 1997, 62, 4457-4464.*
Clausen et al, Journal of Organic Chemistry, 1997, 62, 4457-4464.*
International Peliminary Report on Patentability (Form PCT/IB/373) and Written Opinion of the International Searching Authority (Form PCT/ISA/237) issued on Nov. 2, 2010 in corresponding PCT Application No. PCT/JP2009/055368.
Notification of First Office Action for corresponding Chinese Patent Application No. 200980108746.1, dated Aug. 31, 2012.
International Search Report (PCT/ISA/210) for PCT/JP2009/055368, mailed on Jun. 9, 2009.
Extended European Search Report issued on Feb. 16, 2011 in corresponding European Patent Application No. 09 72 0095.
Notification of Second Office Action for corresponding Chinese Patent Application No. 200980108746.1, dated Jan. 28, 2013.

* cited by examiner

*Primary Examiner* — Johann R Richter
*Assistant Examiner* — Pancham Bakshi
(74) *Attorney, Agent, or Firm* — Birch, Stewart, Kolasch & Birch, LLP

(57) ABSTRACT

The present invention relates to a functional substance-releasing agent containing a silicic acid ester compound represented by formula (1) below, a process for producing the functional substance-releasing agent, and a composition containing the functional substance-releasing agent.

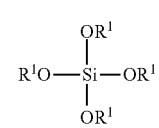

(1)

wherein $R^1$ represents a residue of an alcohol which results from removal of one hydroxyl group therefrom, the alcohol being selected from a functional alcohol having a log P value of 2.0 or less and an alcohol having a log P value of 2.1 or more, a plurality of $R^1$s may be the same or different, provided that the silicic acid ester compound has, in one molecule, at least one residue resulting from removal of one hydroxyl group from a functional alcohol having a log P value of 2.0 or less and at least one residue resulting from removal of one hydroxyl group from an alcohol having a log P value of 2.1 or more.

13 Claims, No Drawings

FUNCTIONAL SUBSTANCE-RELEASING AGENT

FIELD OF THE INVENTION

The present invention relates to a functional substance-releasing agent containing a silicic acid ester compound, which releases a functional substance such as a fragrance, an antibacterial agent and an antifungal agent useful to be incorporated into various products, a process for producing the same, and a composition containing the functional substance-releasing agent.

BACKGROUND OF THE INVENTION

In a blended fragrance, a desired aroma is created by blending a large number of aromatic components so-called top note, middle note and base note having different volatility. During use of this blended fragrance, components having higher volatility vaporize in priority and, as a result, the aroma of the blended fragrance changes with the lapse of time, thus posing a problem in that the aroma cannot be maintained constantly for a prolonged period of time. A gel-like aromatic composition in which a fragrance is included in microcapsules and dispersed in a gel base material is known as a means for solving such a problem (JP-A 63-260567). Though this method is effective in gel-like preparations, a fragrance cannot be stably compounded in liquid preparations having low viscosity due to generation of floating and precipitation of microcapsules.

A knitted cloth-treating composition, a detergent composition and a fragrance, which use silicic acid esters between a fragrance alcohol and an organic silicon compound such as methyltriethoxysilane, are also known (JP-A 54-59498, JP-A 54-93006, and JP-A 58-22063). However, these compositions are so low in hydrophobicity that the decomposition of the silicic acid esters proceeds in aqueous products such as detergents and fragrances, and thus their effect is not continued.

Meanwhile, a silicic acid ester mixture containing polyalkoxysiloxane having such higher hydrolysis resistance as to be mixable in products such as water-containing detergents is known (JP-A 2003-526644). However, this silicic acid ester mixture contains the high-molecular-weight compound, and thus the mixture when blended in various products such as detergents and fragrances is problematic in blending performance such as solubility.

Not only fragrances undergo decomposition in the above products, but volatile antibacterial and antifungal agents also have the same problem, and durability of their effects and blending performance are hardly simultaneously attained.

SUMMARY OF THE INVENTION

The present invention provides a functional substance-releasing agent, containing a silicic acid ester compound represented by the following formula (1):

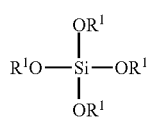

wherein $R^1$ represents a residue of an alcohol which results from removal of one hydroxyl group therefrom, the alcohol being selected from a functional alcohol having a log P value of 2.0 or less and an alcohol having a log P value of 2.1 or more, and a plurality of $R^1$s may be the same as or different from each other, provided that the silicic acid ester compound has, in one molecule, at least one residue resulting from removal of one hydroxyl group from a functional alcohol having a log P value of 2.0 or less and at least one residue resulting from removal of one hydroxyl group from an alcohol having a log P value of 2.1 or more.

The present invention provides a composition containing the functional substance-releasing agent.

The present invention provides a process for producing the functional substance-releasing agent, which includes carrying out an ester exchange reaction between an alkoxysilane represented by the following formula (2) and a mixture of a functional alcohol having a log P value of 2.0 or less and an alcohol having a log P value of 2.1 or more,

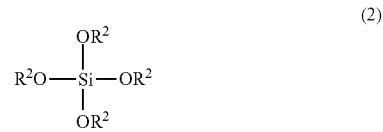

wherein $R^2$ represents an alkyl group having 1 to 6 carbon atoms, and a plurality of $R^2$s may be the same or different.

The present invention provides use of the silicic acid ester compound represented by the following formula (1) as a functional substance-releasing agent.

DETAILED DESCRIPTION OF THE INVENTION

The present invention provides a functional substance-releasing agent which can be blended stably irrespective of its preparation form or intended use, is excellent in storage stability, and can persistently release a functional substance constantly for a prolonged period of time in a system where it is actually used, a process for producing the same, and a composition containing the functional substance-releasing agent.

The functional substance-releasing agent of the present invention can be blended stably irrespective of its preparation form or intended use, is excellent in storage stability, and can persistently release a functional substance constantly for a prolonged period of time in a system where it is actually used. The composition containing the functional substance-releasing agent according to the present invention is excellent in storage stability, can sustain the release of a functional substance such as fragrance alcohol or antimicrobial alcohol for a prolonged period of time, and can sustain aromas and antibacterial properties constantly for a prolonged period of time.

In the silicic acid ester compound (1), $R^1$ represents the residue of an alcohol which results from removal of one hydroxyl group therefrom, the alcohol being selected from a functional alcohol having a log P value of 2.0 or less and an alcohol having a log P value of 2.1 or more, wherein a plurality of $R^1$s may be the same or different, provided the silicic acid ester compound has, in one molecule, at least one residue resulting from removal of one hydroxyl group from a functional alcohol having a log P value of 2.0 or less and at least one residue resulting from removal of one hydroxyl group from an alcohol having a log P value of 2.1 or more.

In the present invention, log P is a 1-octanol/water distribution coefficient of a chemical substance and refers to a value determined from calculation by an f-value method (hydrophobic fragment constant method). In the present invention, log P value (referred to hereinafter as log $P_1$) according to CLOGP Reference Manual Daylight Software 4.34, Albert Leo, David Weininger, Version 1, March 1994, or log P value (referred to hereinafter as log $P_2$) according to Chem Draw Ultra ver. 7.0.1 by Cambridge Soft Company, was used.

The functional alcohol that forms $R^1$ includes fragrance alcohol that is a blended fragrance component, antibacterial alcohol having antibacterial and antifungal properties, moisturizing alcohol having moisturizing property, physiologically active alcohol having physiological activity, coloring alcohol having colorability, and surface-modifying alcohol having general surface activity, among which the fragrance alcohol and antibacterial alcohol are preferable, and the fragrance alcohol is more preferable.

Specific examples of the functional alcohol having a log P value of 2.0 or less includes n-hexanol (log $P_2$, 1.9), trans-2-hexenol (log $P_1$, 1.4), leaf alcohol (cis-3-hexenol, log $P_1$, 1.4), hydroxy citronellol (log $P_1$, 1.5), 3,7-dimethyl-7-methoxyoctan-2-ol (log $P_2$, 2.0), benzyl alcohol (log $P_1$, 1.1), 2-phenylethyl alcohol (log $P_1$, 1.2), γ-phenylpropyl alcohol (log $P_1$, 1.7), cinnamic alcohol (log $P_1$, 1.4), anisic alcohol (log $P_1$, 1.0), methylphenyl carbinol (log $P_1$, 1.2), dimethylphenyl carbinol (log $P_2$, 1.8), dimethylphenylethyl carbinol (log $P_1$, 2.0), phenoxyethyl alcohol (log $P_1$, 1.2), styrallyl alcohol (log $P_1$, 1.41), vanillin (log $P_2$, 1.3), ethyl vanillin (log $P_1$, 1.8), hinokitiol (log $P_2$, 1.9), tri(hydroxymethyl)nitromethane (log $P_2$, −0.87), 2-bromo-2-nitropropane-1,3-diol (log $P_2$, −0.53), 1,3-bis(hydroxymethyl)-5,5'-dimethylhydantoin (log $P_2$, −0.33), and hexahydro-1,3,5-tris(hydroxyethyl)-S-triazine (long $P_2$, −0.11. Among them, those functional alcohols having a log P value of 1.0 to 2.0 are preferable.

The alcohol having a log P value of 2.1 or more includes a functional alcohol having a log P value of 2.1 or more and an aliphatic alcohol having 7 or more carbon atoms.

Specific examples of the functional alcohol having a log P value of 2.1 or more include 3-octanol (log $P_1$, 2.7), 1-octen-3-ol (log $P_1$, 2.2), 2,6-dimethyl-2-heptanol (log $P_1$, 3.0), 2,4-dimethyl-3-cyclohexene-1-methanol (log $P_1$, 2.4), 4-isopropylcyclohexanol (log $P_1$, 2.7), 4-isopropylcyclohexyl methanol (log $P_1$, 3.3), 1-(4-isopropylcyclohexyl)ethanol (log $P_1$, 3.6), p-tert-butylcyclohexanol (log $P_1$, 3.1), o-tert-butylcyclohexanol (log $P_1$, 3.1), 4-methyl-3-decen-5-ol (log $P_1$, 3.7), 9-decenol (log $P_1$, 3.5), 10-undecenol (log $P_1$, 4.0), linalool (log $P_1$, 2.6), geraniol (log $P_1$, 2.8), nerol (log $P_1$, 2.8), citronellol (log $P_1$, 3.3), rhodinol (log $P_1$, 3.3), dimethyloctanol (log $P_1$, 3.5), tetrahydrogeraniol (log $P_1$, 3.7), tetrahydrolinalool (log $P_1$, 3.5), lavandulol (log $P_1$, 2.6), mugol (log $P_1$, 3.0), myrcenol (log $P_1$, 3.0), terpineol (log $P_1$, 2.6), L-menthol (log $P_1$, 3.2), borneol (log $P_1$, 2.6), isopulegol (log $P_1$, 2.8), tetrahydromugol (log $P_1$, 3.5), nopol (log $P_1$, 2.7), farnesol (log $P_1$, 4.8), nerolidol (log $P_1$, 4.6), ambrinol (log $P_1$, 3.8), 1-(2-tert-butylcyclohexyloxy)-2-butanol (log $P_1$, 4.0), pentamethylcyclohexyl propanol (log $P_1$, 5.2), 1-(2,2,6-trimethylcyclohexyl)-3-hexanol (log $P_1$, 5.9), santalol (log $P_1$, 3.9), 3-methyl-5-(2,2,3-trimethyl-3-cyclopenten-1-yl)-2-pentanol (log $P_2$, 4.7), 2-ethyl-4-(2,2,3-trimethyl-3-cyclopenten-1-yl)-2-butenol (log $P_2$, 4.6), 2-methyl-4-(2,2,3-trimethyl-3-cyclopenten-1-yl)-2-buten-1-ol (log $P_1$, 3.9), 2-methyl-4-(2,2,3-trimethyl-3-cyclopenten-1-yl)-1-butanol (log $P_2$, 4.4), 3-methyl-5-(2,2,3-trimethyl-3-cyclopenten-1-yl)-4-penten-2-ol (log $P_2$, 4.2), 3,3-dimethyl-5-(2,2,3-trimethyl-3-cyclopenten-1-yl)-4-penten-2-ol (log $P_2$, 4.6), cedrol (log $P_1$, 4.5), vetiverol (log $P_1$, 4.2), patchouli alcohol (log $P_1$, 5.1), dimethylbenzyl carbinol (log $P_1$, 3.0), thymol (log $P_1$, 3.4), carvacrol (log $P_1$, 3.4), eugenol (log $P_1$, 2.4), isoeugenol (log $P_1$, 2.6), metha-chloroxylenol (log $P_2$, 3.1), 2,4-dichlorophenol (log $P_2$, 3.0), 2,4-dichlorobenzyl alcohol (log $P_2$, 2.5), 3-methyl-4-isopropylphenol (log $P_1$, 3.4), 2,2-dimethyl-3-(3-methylphenyl)propanol (log $P_2$, 3.0), 3-methyl-5-phenylpentanol (log $P_1$, 3.2), phenylethylmethylethyl carbinol (log $P_1$, 3.0), trichlosan (log $P_2$, 5.5), capsaicin (log $P_2$, 3.8), tocopherol (log $P_2$, 13.0), and glycerol monolaurate (log $P_2$, 4.0). Among them, those functional alcohols having a log P of 2.4 to 5 are preferable.

The aliphatic alcohol having 7 or more carbon atoms is preferably an aliphatic alcohol having 10 to 22 carbon atoms, more preferably an aliphatic alcohol having 12 to 20 carbon atoms, even more preferably an aliphatic alcohol having 14 to 18 carbon atoms, from the viewpoint of smell and reactivity. Preferable examples of the aliphatic alcohol having 7 or more carbon atoms can include decanol (log $P_2$, 4.0), isodecanol (log $P_2$, 3.9), undecanol (log $P_2$, 4.5), lauryl alcohol (log $P_2$, 5.1), tridecanol (log $P_2$, 5.6), myristyl alcohol (log $P_2$, 6.1), palmityl alcohol (log $P_2$, 7.2), stearyl alcohol (log $P_2$, 8.2), methyl-branched or Guerbet-type isostearyl alcohol (log $P_2$, 8.1), oleyl alcohol (log $P_2$, 7.3), eicosanol (log $P_2$, 9.3), 2-octyl-1-dodecanol (log $P_2$, 9.2), 3,7,11,15-tetramethyl-2-hexadecenol (log $P_2$, 8.5), and docosanol (log $P_2$, 10.3).

When the functional alcohol in the present invention has an aldehyde group in its molecule, a reaction can be generated among functional alcohol molecules during production or after release from the functional substance-releasing agent, to reduce the yield or prevent the functional alcohol molecules from efficiently exhibiting their functions. Accordingly, the functional alcohol in the present invention is preferably the one not having an aldehyde group in its molecule, from the viewpoint of inhibiting the reaction among functional alcohol molecules.

The content of the silicic acid ester compound (1) in the functional substance-releasing agent of the present invention is preferably 3 to 100% by mass, more preferably 10 to 95% by mass, from the viewpoint of constant sustained release of a functional substance for a prolonged period of time.

The functional substance-releasing agent of the present invention may, besides the silicic acid ester compound (1), contain byproducts produced, or raw materials used, in production of the silicic acid ester compound (1).

The functional substance-releasing agent of the present invention can be produced by the following process 1 or 2.

Process 1:

A process which includes ester exchange reaction between an alkoxysilane represented by the following formula (2) (referred to hereinafter as alkoxysilane (2)) and a mixture of a functional alcohol having a log P value of 2.0 or less and an alcohol having a log P value of 2.1 or more.

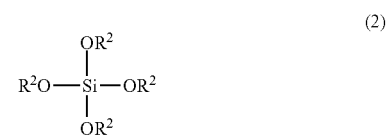

wherein $R^2$ represents an alkyl group having 1 to 6 carbon atoms, and a plurality of $R^2$s may be the same or different.

Process 2:

A process which includes esterification reaction between a halogenated silane represented by the following formula (3) (referred to hereinafter as halogenated silane (3)) and a mixture of a functional alcohol having a log P value of 2.0 or less and an alcohol having a log P value of 2.1 or more.

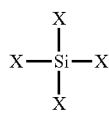

(3)

wherein X represents a halogen atom.

The composition of alcohols introduced into molecules of the silicic acid ester compound (1) varies depending on the molar ratio of the functional alcohol having a log P value of 2.0 or less to the alcohol having a log P value of 2.1 or more in the alcohol mixture of a functional alcohol having a log P value of 2.0 or less and an alcohol having a log P value of 2.1 or more used in the processes 1 and 2. As the ratio of the alcohol having a log P value of 2.1 or more increases, storage stability is improved, while as the ratio of the functional alcohol having a log P value of 2.0 or less increases, the functional substance can be released sustainably for a prolonged period of time. From this viewpoint, the molar ratio of the functional alcohol having a log P value of 2.0 or less/the alcohol having a log P value of 2.1 or more is preferably from 95/5 to 5/95.

In the alkoxysilane (2) used in the process 1, $R^2$ is preferably a methyl or ethyl group, more preferably an ethyl group, from the viewpoint of availability etc.

In the process 1, the molar ratio of the alcohol mixture to the alkoxysilane (2) is preferably 0.1 to 10, more preferably 0.5 to 7, even more preferably 1 to 5.

The reaction temperature in the ester exchange reaction in the process 1 is preferably not higher than the boiling points of the alkoxysilane (2) and the alcohols, more preferably room temperature (20° C.) to 200° C., even more preferably 50 to 170° C., even more preferably 70 to 150° C., and even more preferably 90 to 130° C. The ester exchange reaction in the process 1 is conducted preferably under reduced pressure, from the viewpoint of enabling rapid progress of the reaction, etc. The degree of depressurization, although varying depending on the reaction temperature which may be not higher than the boiling points of the alkoxysilane (2) and the alcohols, is preferably 1.3 Pa to ordinary pressure (0.1 MPa), more preferably 130 Pa to 40 kPa, even more preferably 1.3 kPa to 13 kPa. The reaction may be carried out under reduced pressure from the start, or may be carried out at pressure reduced in the middle of the reaction.

In the ester exchange reaction in the process 1, addition of a catalyst is preferable from the viewpoint of enabling rapid progress of the reaction, etc. The catalyst that can be used herein include alkali catalysts such as sodium hydroxide, potassium hydroxide, sodium methoxide, sodium ethoxide, potassium methoxide, and potassium ethoxide, and Lewis acid catalysts such as aluminum tetraisopropoxide and titanium tetraisopropoxide.

The halogen atom in the halogenated silane (3) used in the process 2 includes a chlorine atom, a bromine atom, an iodine atom etc., among which a chlorine atom is preferable.

In the esterification reaction between the halogenated silane (3) and the alcohol mixture in the process 2, the molar ratio of the alcohol mixture to the halogenated silane (3) is preferably 0.1 to 10, more preferably 0.5 to 7, even more preferably 1 to 5.

Since an acid is produced as byproduct with progress of the reaction in the process 2, a base is preferably added for the reaction. Examples of the used base include tertiary amines (for example, triethylamine), and pyridine.

In the esterification reaction in the process 2, a solvent may be used from the viewpoint of production of a salt as byproduct in a large amount, etc. The reaction can be carried out at a low temperature at which the substrate and solvent do not coagulate. If the solvent should be removed after completion of the reaction, various apparatuses and facilities known in the art can be used. For desalting, known methods such as filtration, extraction and electrodialysis can be used.

The functional substance-releasing agent of the present invention obtained by the ester exchange reaction in the process 1 or by the esterification reaction in the process 2 may, besides the silicic acid ester compound (1), contain silicic acid ester compounds different in the degree of substitution, and may further contain linear or cyclic (poly) condensates having siloxane molecules condensed therein.

The functional substance-releasing agent of the invention containing the silicic acid ester compound (1) can sustainably release its functional substance for a prolonged period of time. When the functional alcohol residue represented by $R^1$ in the silicic acid ester compound (1) is a residue derived by removing one hydroxyl group from fragrance alcohol or antibacterial alcohol, the functional substance-releasing agent of the present invention can maintain an aroma or antimicrobial property for a prolonged period of time and is useful as an aroma-sustaining agent or an antimicrobial property-sustaining agent.

The functional substance-releasing agent of the present invention can be incorporated into various products. The functional substance-releasing agent can be used in not only non-aqueous products, for example sanitary products such as oil-based deodorants, powder detergents, solid soaps, bath agents, and diapers, and deodorants such as aerosols, but also in perfumes, Colognes and aqueous deodorants because of its excellent storage stability in aqueous solutions, as well as in products for clothing such as liquid detergents and softeners, dishwashing detergents, cosmetic products such as liquid soaps and face lotions, products for hair such as shampoos, rinses, conditioners and hair dressings, liquid bath agents, etc., and the functional alcohol therein can be released for a prolonged period of time.

The composition of the present invention containing the functional substance-releasing agent of the present invention can be used as a detergent composition, a softener composition, an aromatic composition and a deodorant composition.

The content of the functional substance-releasing agent in the composition of the present invention is not particularly limited and can vary considerably depending on its intended use. When the composition of the present invention is used as a detergent composition or a softener composition, the content of the functional substance-releasing agent in the composition is preferably 0.001 to 10% by mass, more preferably 0.01 to 5% by mass. When the composition of the present invention is used as an aromatic composition, the content of the functional substance-releasing agent in the composition is preferably 0.001 to 90% by mass, more preferably 0.01 to 10% by mass. When the composition of the present invention is used as a deodorant composition, the content of the functional substance-releasing agent in the composition is preferably 0.0001 to 10% by mass, more preferably 0.001 to 5% by mass.

EXAMPLES

The present invention is described in detail with reference to the Examples. The Examples are merely illustrative of the present invention and are not intended to limit the present invention.

Synthesis Example 1

Synthesis of a Functional Substance-Releasing Agent Containing a Mixed Silicic Acid Ester of 2-phenylethyl alcohol (Log $P_1$, 1.2) and geraniol (Log $P_1$, 2.8) (1:1)

A 200-mL four-neck flask was charged with 37.51 g (0.18 mol) of tetraethoxysilane, 39.61 g (0.32 mol) of 2-phenylethyl alcohol, 50.05 g (0.32 mol) of geraniol, and 0.671 mL of 2.8% solution of sodium methoxide in methanol, and the mixture was stirred at 109 to 120° C. for about 2 hours while ethanol was distilled away in a nitrogen stream. After 2 hours, the pressure in the flask was reduced gradually to 8 kPa, and the mixture was stirred at about 120° C. for additional 4 hours while ethanol was distilled away. After 4 hours, the reaction mixture was cooled, released from depressurization, and then filtered to give 96.55 g yellow oily matter containing a mixed silicic acid ester of 2-phenylethyl alcohol and geraniol in a molar ratio of 1:1. The obtained oily matter was analyzed by gas chromatography to give a functional substance-releasing agent having the composition shown in Table 1.

TABLE 1

| GC analysis results in Synthesis Example 1*[1] | area % |
|---|---|
| Si(OEt)$_2$(OEtPh)(OGer) | 2.0 |
| Si(OEt)(OEtPh)$_2$(OGer) | 9.4 |
| Si(OEt)(OEtPh)(OGer)$_2$ | 10.1 |
| Si(OEtPh)$_3$(OGer) | 15.0 |
| Si(OEtPh)$_2$(OGer)$_2$ | 23.6 |
| Si(OEtPh)(OGer)$_3$ | 16.5 |
| Others | 23.4 |

*[1]Et is an ethyl group, EtPh is a residue derived from 2-phenylethyl alcohol by removing a hydroxyl group, and Ger is a residue derived from geraniol by removing a hydroxyl group; this applies hereinafter.

Synthesis Example 2

Synthesis of a Functional Substance-Releasing Agent Containing a Mixed Silicic Acid Ester of 2-phenylethyl alcohol and Sandalmysore Core (Log $P_1$, 3.9) (1:1)

A 100-mL four-neck flask was charged with 18.78 g (90 mmol) of tetraethoxysilane, 19.81 g (0.16 mol) of 2-phenylethyl alcohol, 31.52 g (0.16 mol) of Sandalmysore core (2-methyl-4-(2,2,3-trimethyl-3-cyclopenten-1-yl)-2-buten-1-ol, manufactured by Kao Corporation), and 0.635 mL of 2.8% solution of sodium methoxide in methanol, and the mixture was stirred at 109 to 110° C. for about 2 hours while ethanol was distilled away in a nitrogen stream. After 2 hours, the pressure in the flask was reduced gradually to 8 kPa, and the mixture was stirred at about 120° C. for additional 3 hours while ethanol was distilled away. After 3 hours, the reaction mixture was cooled, released from depressurization, and then filtered to give 54.04 g yellow oily matter containing a mixed silicic acid ester of 2-phenylethyl alcohol and Sandalmysore core in a molar ratio of 1:1. The obtained oily matter was analyzed by gas chromatography to give a functional substance-releasing agent having the composition shown in Table 2.

TABLE 2

| GC analysis results in Synthesis Example 2*[1] | area % |
|---|---|
| Si(OEt)$_2$(OEtPh)(OSMC) | 1.6 |
| Si(OEt)(OEtPh)$_2$(OSMC) | 7.9 |
| Si(OEt)(OEtPh)(OSMC)$_2$ | 9.7 |
| Si(OEtPh)$_3$(OSMC) | 13.1 |
| Si(OEtPh)$_2$(OSMC)$_2$ | 20.6 |
| Si(OEtPh)(OSMC)$_3$ | 14.2 |
| Others | 32.9 |

*[1]SMC is a residue derived by removing a hydroxyl group from 2-methyl-4-(2,2,3-trimethyl-3-cyclopenten-1-yl)-2-buten-1-ol.

Synthesis Example 3

Synthesis of a Functional Substance-Releasing Agent Containing a Mixed Silicic Acid Ester of 2-phenylethyl alcohol and myristyl alcohol (Log $P_2$, 6.1) (3:1)

A 100-mL four-neck flask was charged with 16.22 g (78 mmol) of tetraethoxysilane, 25.69 g (0.21 mol) of 2-phenylethyl alcohol, 15.00 g (70 mmol) of myristyl alcohol, and 0.486 mL of 2.8% solution of sodium methoxide in methanol, and the mixture was stirred at 107 to 118° C. for about 3 hours while ethanol was distilled away in a nitrogen stream. After 3 hours, the pressure in the flask was reduced gradually to 8 kPa, and the mixture was stirred at about 120° C. for additional 5 hours while ethanol was distilled away. After 5 hours, the reaction mixture was cooled, released from depressurization, and then filtered to give 42.98 g yellow oily matter containing a mixed silicic acid ester of 2-phenylethyl alcohol and myristyl alcohol in a molar ratio of 3:1. The obtained oily matter was analyzed by gas chromatography to give a functional substance-releasing agent having the composition shown in Table 3.

TABLE 3

| GC analysis results in Synthesis Example 3 | area % |
|---|---|
| Si(OEt)$_2$(OEtPh)(OC$_{14}$H$_{29}$) | 1.8 |
| Si(OEt)(OEtPh)$_2$(OC$_{14}$H$_{29}$) | 11.7 |
| Si(OEt)(OEtPh)(OC$_{14}$H$_{29}$)$_2$ | 4.9 |
| Si(OEtPh)$_3$(OC$_{14}$H$_{29}$) | 26.2 |
| Si(OEtPh)$_2$(OC$_{14}$H$_{29}$)$_2$ | 15.4 |
| Si(OEtPh)(OC$_{14}$H$_{29}$)$_3$ | 4.1 |
| Others | 35.9 |

Synthesis Example 4

Synthesis of a Functional Substance-Releasing Agent Containing a Mixed Silicic Acid Ester of 2-phenylethyl alcohol and myristyl alcohol (1:1)

A 100-mL four-neck flask was charged with 13.53 g (65 mmol) of tetraethoxysilane, 14.24 g (0.12 mol) of 2-phenylethyl alcohol, 25.00 g (0.12 mol) of myristyl alcohol, and 0.342 mL of 2.8% solution of sodium methoxide in methanol, and the mixture was stirred at about 120° C. for about 2.5 hours while ethanol was distilled away in a nitrogen stream. After 2.5 hours, the pressure in the flask was reduced gradually to 8 kPa, and the mixture was stirred at about 118° C. for additional 6 hours while ethanol was distilled away. After 6 hours, the reaction mixture was cooled, released from depressurization, and then filtered to give 41.30 g yellow oily matter containing a mixed silicic acid ester of 2-phenylethyl alcohol and myristyl alcohol in a molar ratio of 1:1. The obtained oily matter was analyzed by gas chromatography to give a functional substance-releasing agent having the composition shown in Table 4.

TABLE 4

| GC analysis results in Synthesis Example 4 | area % |
|---|---|
| $Si(OEt)_2(OEtPh)(OC_{14}H_{29})$ | 2.1 |
| $Si(OEt)(OEtPh)_2(OC_{14}H_{29})$ | 9.1 |
| $Si(OEt)(OEtPh)(OC_{14}H_{29})_2$ | 11.1 |
| $Si(OEtPh)_3(OC_{14}H_{29})$ | 13.3 |
| $Si(OEtPh)_2(OC_{14}H_{29})_2$ | 23.3 |
| $Si(OEtPh)(OC_{14}H_{29})_3$ | 17.9 |
| Others | 23.2 |

Synthesis Example 5

Synthesis of a Functional Substance-Releasing Agent Containing a Mixed Silicic Acid Ester of 2-phenylethyl alcohol and stearyl alcohol (log $P_2$, 8.2) (3:1)

A 100-mL four-neck flask was charged with 14.54 g (70 mmol) of tetraethoxysilane, 23.04 g (0.19 mol) of 2-phenylethyl alcohol, 17.00 g (63 mmol) of stearyl alcohol, and 0.460 mL of 2.8% solution of sodium methoxide in methanol, and the mixture was stirred at about 103° C. for about 4 hours while ethanol was distilled away in a nitrogen stream. After 4 hours, the pressure in the flask was reduced gradually to 8 kPa, and the mixture was stirred for additional 4 hours while ethanol was distilled away. After 4 hours, the reaction mixture was cooled, released from depressurization, and then filtered to give 42.02 g yellow oily matter containing a mixed silicic acid ester of 2-phenylethyl alcohol and stearyl alcohol in a molar ratio of 3:1. The obtained oily matter was analyzed by gas chromatography to give a functional substance-releasing agent having the composition shown in Table 5.

TABLE 5

| GC analysis results in Synthesis Example 5 | area % |
|---|---|
| $Si(OEt)_2(OEtPh)(OC_{18}H_{37})$ | 1.7 |
| $Si(OEt)(OEtPh)_2(OC_{18}H_{37})$ | 12.1 |
| Others*[1] | 86.2 |

*[1] A mixture containing $Si(OEtPh)_3(OC_{18}H_{37})$, $Si(OEtPh)_2(OC_{18}H_{37})_2$, and $Si(OEtPh)(OC_{18}H_{37})_3$.

Synthesis Example 6

Synthesis of a Functional Substance-Releasing Agent Containing a Mixed Silicic Acid Ester of 2-phenylethyl alcohol and stearyl alcohol (1:1)

A 100-mL four-neck flask was charged with 11.54 g (55 mmol) of tetraethoxysilane, 12.18 g (0.10 mol) of 2-phenylethyl alcohol, 27.00 g (0.10 mol) of stearyl alcohol, and 0.306 mL of 2.8% solution of sodium methoxide in methanol, and the mixture was stirred at about 101° C. for about 3 hours while ethanol was distilled away in a nitrogen stream. After 3 hours, the pressure in the flask was reduced gradually to 8 kPa, and the mixture was stirred for additional 4.5 hours while ethanol was distilled away. After 4.5 hours, the reaction mixture was cooled, released from depressurization, and then filtered to give 40.48 g yellow oily matter containing a mixed silicic acid ester of 2-phenylethyl alcohol and stearyl alcohol in a molar ratio of 1:1. The obtained oily matter was analyzed by gas chromatography to give a functional substance-releasing agent having the composition shown in Table 6.

TABLE 6

| GC analysis results in Synthesis Example 6 | area % |
|---|---|
| $Si(OEt)_2(OEtPh)(OC_{18}H_{37})$ | 2.0 |
| $Si(OEt)(OEtPh)_2(OC_{18}H_{37})$ | 9.4 |
| Others*[1] | 88.6 |

*[1] A mixture containing $Si(OEtPh)_3(OC_{18}H_{37})$, $Si(OEtPh)_2(OC_{18}H_{37})_2$, and $Si(OEtPh)(OC_{18}H_{37})_3$.

Synthesis Example 7

Synthesis of a Functional Substance-Releasing Agent Containing a Mixed Silicic Acid Ester of cis-3-hexenol (log $P_1$, 1.4) and geraniol (log $P_1$, 2.8) (1:1)

A 100-mL four-neck flask was charged with 25.03 g (0.12 mol) of tetraethoxysilane, 21.63 g (0.22 mol) of cis-3-hexenol, 33.36 g (0.22 mol) of geraniol, and 0.45 mL of 2.8% solution of sodium methoxide in methanol, and the mixture was stirred at 100 to 120° C. for about 2.5 hours while ethanol was distilled away in a nitrogen stream. After 2.5 hours, the pressure in the flask was reduced gradually to 8 kPa, and the mixture was stirred at 114 to 120° C. for additional 3 hours while ethanol was distilled away. After 3 hours, the reaction mixture was cooled, released from depressurization, and then filtered to give 59.00 g yellow oily matter containing a mixed silicic acid ester of cis-3-hexenol and geraniol in a molar ratio of 1:1. The obtained oily matter was analyzed by gas chromatography to give a functional substance-releasing agent having the composition shown in Table 7.

TABLE 7

| GC analysis results in Synthesis Example 7*¹ | area % |
| --- | --- |
| Si(OEt)$_2$(OHex)(OGer) | 2.0 |
| Si(OEt)(OHex)$_2$(OGer) | 9.0 |
| Si(OEt)(OHex)(OGer)$_2$ | 10.7 |
| Si(OHex)$_3$(OGer) | 13.7 |
| Si(OHex)$_2$(OGer)$_2$ | 24.0 |
| Si(OHex)(OGer)$_3$ | 18.4 |
| Others | 22.2 |

*¹Hex represents a residue resulting from removal of a hydroxyl group from cis-3-hexenol.

TABLE 8

| Non-fragrant liquid softener A | Compounding amount (mass %) |
| --- | --- |
| Cationic softening agent[1] | 15 |
| Polyoxyethylene (20) lauryl ether | 3 |
| Calcium chloride | 0.05 |
| Dehydration condensate of 1.7 moles of hardened tallow fatty acid with 1 mole of glycerin | 1 |
| Ethanol | 0.25 |
| Tetrasodium ethylenediaminetetraacetate | 0.01 |
| Conc. hydrochloric acid | Suitable amount |
| Ion-exchanged water | Balance |

[1]A product obtained in a known method by dehydration condensation of N-(3-aminopropyl)-N-(2-hydroxyethyl)-N-methylamine with hardened tallow fatty acid in a molar ratio of 1/1.9.

TABLE 9

| Type of functional substrance-releasing agent | | Example 1 Synthesis example 1 | Example 2 Synthesis example 2 | Example 3 Synthesis example 3 | Example 4 Synthesis example 4 | Example 5 Synthesis example 5 | Example 6 Synthesis example 6 | Comparative example 1 Synthesis example 8 |
| --- | --- | --- | --- | --- | --- | --- | --- | --- |
| Residual ratio of silicic acid etsre compound (%) | After 3 days | 87 | 95 | 91 | 98 | 95 | 99 | 41 |
| | After 7 days | 82 | 90 | 85 | 96 | 91 | 98 | 11 |

Synthesis Example 8

Synthesis of a Functional Substance-Releasing Agent Containing tetrakis(2-phenylethyl) Silicic Acid Ester (tetrakis(2-phenylethyloxy)silane)

A 200-mL four-neck flask was charged with 41.68 g (0.20 mol) of tetraethoxysilane, 87.98 g (0.72 mol) of 2-phenylethyl alcohol, and 1.85 mL of 2.8% solution of sodium methoxide in methanol, and the mixture was stirred at 112° C. to 118° C. for about 2 hours while ethanol was distilled away in a nitrogen stream. After 2 hours, the pressure in the flask was reduced gradually to 8 kPa, and the mixture was stirred for additional 3 hours while ethanol was distilled away. After 3 hours, the reaction mixture was cooled, released from depressurization, and then filtered to give 95.04 g yellow oily matter containing tetrakis(2-phenylethyl) silicic acid ester.

Examples 1 to 6

Comparative Example 1

Non-fragrant liquid softener A shown in Table 8 was prepared in a usual manner. Each of the functional substance-releasing agents obtained in Synthesis Examples 1 to 6 and the comparative functional substance-releasing agent obtained in Synthesis Example 8, and the non-fragrant liquid softener A, were introduced into a 50-mL screw tube (Maru M No. 7) such that the amount of the functional substance-releasing agent reached 0.5% by mass based on the non-fragrant liquid softener A. The resulting mixture was heated to 50° C. and then cooled to prepare a softener composition. This softener composition was sealed and stored in a thermostatic bath at 40° C. After 3 days and after 7 days, the amount of 2-phenylethyl alcohol therein was measured by HPLC (detector: UV) to determine the residual ratio of the silicic acid ester compound. The results are shown in Table 9.

As can be seen from Table 9, the functional substance-releasing agent of the present invention can be used to obtain a composition excellent in storage stability.

Examples 7 to 9

Comparative Example 2

Each of the functional substance-releasing agents of the present invention obtained in Synthesis Examples 1, 2 and 5 and the comparative functional substance-releasing agent obtained in Synthesis Example 8 was added in an amount shown in Table 10 to the non-fragrant liquid softener A shown in Table 8, to prepare a softener composition in the same manner as in Example 1. The softener composition was evaluated for the durability of aroma before and after storage for 2 weeks at 40° C. The results are shown in Table 10.

<Method of Evaluating the Durability of Aroma>

24 cotton towels were previously washed repeatedly 5 times with a commercially available weakly alkaline detergent (Attack, manufactured by Kao Corporation) in a fully automatic washing machine NW-6CY manufactured by Hitachi, Ltd., and then dried in a room to remove an excess of the detergent (detergent concentration: 0.0667% by mass, using 47 L (20° C.) of tap water, washing (10 minutes)-rinsing (twice) in water).

5 L tap water was poured into a National electric bucket N-BK2-A, then each softener composition before and after storage for 2 weeks at 40° C. was dissolved therein in an amount of 10 g softener composition/1.0 kg clothing (preparation of a treatment bath), and 1 minute thereafter, 2 cotton towels pretreated by the method described above were treated by immersion for 5 minutes in the treatment bath. After immersion treatment, the 2 cotton towels were transferred to a National electric washing machine NA-35 and subjected to dewatering for 3 minutes. After dewatering, each towel was left overnight in a room at about 20° C., and the towel after drying was folded into eight and left in a room at about 20° C. for 1 week.

The towels after dewatering, after overnight drying, and after left for 1 week, respectively, were evaluated sensorily for the intensity of phenylethyl alcohol aroma by a panel of 10 specialists under the following criteria, to determine the average. ⊚ was given when the average was 3; ○, when the average was 2.0 or more to less than 3.0; Δ, when the average was 1.0 or more to less than 2.0; and x, when the average was 0 or more to less than 1.0.

Evaluation Criteria:
3: The aroma of phenylethyl alcohol is strong.
2: The aroma of phenylethyl alcohol can be recognized.
1: The aroma of phenylethyl alcohol cannot be recognized, but some aroma can be sensed.
0: The aroma of phenylethyl alcohol is absent.

TABLE 10

| Type of functional substrate releasing agent | Example 7 Synthesis example 1 | | Example 8 Synthesis example 2 | | Example 9 Synthesis example 5 | | Comparative example 2 Synthesis example 8 | |
|---|---|---|---|---|---|---|---|---|
| Added amount of functional releasing agent (mass %) | 1.0 | | 1.0 | | 1.0 | | 0.5 | |
| 40° C./2-week storage | Before storage | After storage | Before storage | After storage | Before storage | After storage | Before storage | After storage |
| Results of sensory evaluation — After dewatering | ○ | ○ | ○ | ○ | ○ | ○ | ○ | ⊚ |
| After overnight drying | ○ | ○ | ○ | ○ | ○ | ○ | ○ | Δ |
| After left for 1 week | ○ | ○ | ○ | ○ | ○ | ○ | ○ | X |

From Table 10, it can be seen that in Comparative Example 2, the durability of the aroma was lowered due to decomposition during storage, while the functional substance-releasing agents of the present invention were excellent in storage stability and thus sustained the aroma for a long period of time.

The invention claimed is:

1. A functional substance-releasing agent, comprising a silicic acid ester compound represented by the following formula (1):

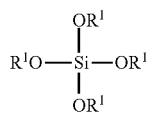

(1)

wherein $R^1$ represents a residue of an alcohol which results from removal of one hydroxyl group therefrom, the alcohol being selected from the group consisting of a functional alcohol having a log P value of 2.0 or less and an alcohol having a log P value of 2.1 or more, and a plurality of $R^1$s may be the same as or different from each other, provided that the silicic acid ester compound has, in one molecule, at least one residue resulting from removal of one hydroxyl group from a functional alcohol having a log P value of 2.0 or less and at least one residue resulting from removal of one hydroxyl group from an alcohol having a log P value of 2.1 or more;
wherein the functional alcohol having a log P value of 2.0 or less is selected from the group consisting of trans-2-hexenol, leaf alcohol, 2-phenylethyl alcohol, cinnamic alcohol and anisic alcohol; and
wherein the alcohol having a log P value of 2.1 or more is selected from the group consisting of 4-methyl-3-decen-5-ol, geraniol, citronellol, 2-methyl-4-(2,2,3-trimethyl-3-cyclopenten-1-yl)-2-buten-1-ol and 2-ethyl-4-(2,2,3-trimethyl-3-cyclopenten-1-yl)-2-butenol.

2. A detergent, softener, aromatic or deodorant composition comprising the functional substance-releasing agent according to claim 1.

3. A process for producing the functional substance-releasing agent according to claim 1, which comprises carrying out an ester exchange reaction between an alkoxysilane represented by the following formula (2) and a mixture of as functional alcohol having a log P value of 2.0 or less and an alcohol having a log P value of 2.1 or more,

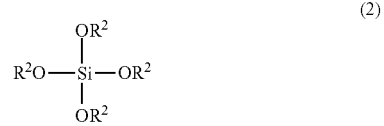

(2)

wherein $R^2$ represents an alkyl group having 1 to 6 carbon atoms, and a plurality of $R^2$s may be the same as or different from each other;
wherein the functional alcohol having a log P value of 2.0 or less is selected from the group consisting of trans-2-hexenol, leaf alcohol, 2-phenylethyl alcohol, cinnamic alcohol and anisic alcohol; and
wherein the alcohol having a log P value of 2.1 or more is selected from the group consisting of 4-methyl-3-decen-5-ol, geraniol, citronellol, 2-methyl-4-(2,2,3-trimethyl-3-cyclopenten-1-yl)-2-buten-1-ol and 2-ethyl-4-(2,2,3-trimethyl-3-cyclopenten-1-yl)-2-butenol.

4. A process for producing the functional substance-releasing agent according to claim 1, which comprises carrying out an esterification reaction between a halogenated silane represented by the following formula (3) and a mixture of a functional alcohol having a log P value of 2.0 or less and an alcohol having a log P value of 2.1 or more,

(3)

wherein X represents a halogen atom;

wherein the functional alcohol having a log P value of 2.0 or less is selected from the group consisting of trans-2-hexenol, leaf alcohol, 2-phenylethyl alcohol, cinnamic alcohol and anisic alcohol; and wherein the alcohol having a log P value of 2.1 or more is selected from the group consisting of 4-methyl-3-decen-5-ol, geraniol, citronellol, 2-methyl-4-(2,2,3-trimethyl-3-cyclopenten-1-yl)-2-buten-1-ol and 2-ethyl-4-(2,2,3-trimethyl-3-cyclopenten-1-yl)-2-butenol.

5. The functional substance-releasing, agent according to claim 1, wherein the functional alcohol having a log P value of 2.0 or less is 2-phenylethyl alcohol or leaf alcohol.

6. The functional substance-releasing agent according to claim 1, wherein the alcohol having a log P value of 2.1 or more is geraniol or 2-methyl-4-(2,2,3-trimethyl-3-cyclopenten-1-yl)-2-buten-1-ol.

7. The functional substance-releasing agent according to claim 1, wherein the functional alcohol having a log P value of 2.0 or less is selected from the group consisting of trans-2-hexenol, leaf alcohol, 2-phenylethyl alcohol, cinnamic, alcohol and anisic alcohol; and the alcohol having a log P value o 2.1 or more is selected from the group consisting of 4-methyl-3-decen-5-ol, geraniol, citronellol and 2-methyl-4-(2,2,3-trimethyl-3-cyclopenten-1-yl)-2-buten-1-ol.

8. The functional substance-releasing agent according to claim 1, wherein the functional alcohol having a log P value of 2.0 or less is selected from the group consisting of leaf alcohol and 2-phenylethyl alcohol; and the alcohol having a log P value 2.1 or more is selected from the group consisting of 4-methyl-3-decen-5-ol, geraniol, citronellol and 2-methyl-4-(2,2,3-trimethyl-3-cyclopenten-1-yl)-2-buten-1-ol.

9. The functional substance-releasing agent according to claim 1, wherein the functional alcohol having a log P value of 2.0 or less is selected from the group consisting of leaf alcohol and 2-phenylethyl alcohol; and the alcohol having a log P value of 2.1 or more is selected from the group consisting of geraniol and 2-methyl-4-(2,2,3-trimethyl-3-cyclopenten-1-yl)-2-buten-1-ol.

10. A detergent composition comprising the functional substance-releasing agent according to claim 1.

11. A softener composition comprising the functional substance-releasing agent according to claim 1.

12. An aromatic composition comprising the functional substance-releasing agent according to claim 1.

13. A deodorant composition comprising the functional substance-releasing agent according to claim 1.

* * * * *